(12) United States Patent
Limmer et al.

(10) Patent No.: US 10,568,597 B2
(45) Date of Patent: Feb. 25, 2020

(54) BEARING CONFIGURATION FOR THE ROTATIONAL MOUNTING OF A COMPONENT PROVIDED FOR ROTATIONAL MOVEMENT, AND MEDICAL EXAMINATION DEVICE INCLUDING THE BEARING CONFIGURATION

(71) Applicant: SIEMENS HEALTHCARE GMBH, Erlangen (DE)

(72) Inventors: Andreas Limmer, Fuerth (DE); Friedrich Schirmer, Buch am Wald (DE)

(73) Assignee: Siemens Healthcare GmbH, Erlangen (DE)

( * ) Notice: Subject to any disclaimer, the term of this patent is extended or adjusted under 35 U.S.C. 154(b) by 552 days.

(21) Appl. No.: 15/439,207

(22) Filed: Feb. 22, 2017

(65) Prior Publication Data

US 2017/0238890 A1   Aug. 24, 2017

(30) Foreign Application Priority Data

Feb. 22, 2016   (DE) .................... 10 2016 202 689

(51) Int. Cl.
*A61B 6/00*  (2006.01)
*F16C 41/00* (2006.01)
*F16C 32/06* (2006.01)

(52) U.S. Cl.
CPC ............ *A61B 6/4441* (2013.01); *A61B 6/467* (2013.01); *A61B 6/548* (2013.01); *F16C 32/0614* (2013.01); *F16C 32/0696* (2013.01); *F16C 41/001* (2013.01); *F16C 2316/10* (2013.01)

(58) Field of Classification Search
CPC .................... A61B 6/4441; F16C 32/0696
See application file for complete search history.

(56) References Cited

U.S. PATENT DOCUMENTS 6,609,826 B1 *   8/2003   Fujii ................... A61B 6/12
                                                378/197

* cited by examiner

*Primary Examiner* — Dani Fox
(74) *Attorney, Agent, or Firm* — Laurence Greenberg; Werner Stemer; Ralph Locher

(57) ABSTRACT

A bearing configuration for the rotational mounting of a component provided for rotational movement includes a positionally fixed sleeve on which the component is rotatably mounted by one or more bearing elements or a plain-bearing. A pressure element is provided in the interior of the sleeve for readily expanding the sleeve and placing the sleeve in frictional contact with the component which is spaced apart from the sleeve by an air gap. A medical examination device having the bearing configuration is also provided.

18 Claims, 3 Drawing Sheets

BEARING CONFIGURATION FOR THE ROTATIONAL MOUNTING OF A COMPONENT PROVIDED FOR ROTATIONAL MOVEMENT, AND MEDICAL EXAMINATION DEVICE INCLUDING THE BEARING CONFIGURATION

CROSS-REFERENCE TO RELATED APPLICATION

This application claims the priority, under 35 U.S.C. §119, of German Patent Application DE 10 2016 202 689.5, filed Feb. 22, 2016; the prior application is herewith incorporated by reference in its entirety.

BACKGROUND OF THE INVENTION

Field of the Invention

The invention relates to a bearing configuration for the rotational mounting of a component provided for rotational movement, including a positionally fixed sleeve on which the component is rotatably mounted by way of one or more bearing elements or in plain-bearing fashion.

A bearing configuration of that type serves for the rotational mounting of a component, that is to say a moving axle can be realized through the use thereof. In the present case, the bearing configuration includes a positionally fixed sleeve which, in effect, forms the bearing axis or axis of rotation. The component is rotatably mounted on the sleeve. That may be realized by way of one or more bearing elements, such as corresponding rolling bearings or the like, although it is alternatively also possible for the component to be mounted in plain-bearing fashion on a correspondingly low-friction sleeve.

Moving axles of that type are braked manually or electrically, depending on the usage situation, in order to hold the previously moved component in a desired position. The braking torque of the axles is dependent on the inertia and on the possibility, defined by the structural space, of providing a suitable braking device. The use of standardized brakes is made difficult, in particular, due to the inertia and the often small amount of available structural space.

Summary of the Invention

It is accordingly an object of the invention to provide a bearing configuration for the rotational mounting of a component provided for rotational movement and a medical examination device including the bearing configuration, which overcome the hereinafore-mentioned disadvantages of the heretofore-known configurations and devices of this general type and in which the bearing configuration, due to a small construction, can be integrated into a correspondingly small structural space, but nevertheless provides high braking torques.

With the foregoing and other objects in view there is provided, in accordance with the invention, a bearing configuration for the rotational mounting of a component provided for rotational movement, comprising a positionally fixed sleeve on which the component is rotatably mounted by way of one or more bearing elements or in plain-bearing fashion. A pressure element is provided in the interior of the sleeve, by way of which the sleeve can be radially expanded and placed in frictional contact with the component which is spaced apart by way of an air gap.

In the case of the bearing configuration according to the invention, the positionally fixed sleeve not only serves for defining the bearing axis or axis of rotation itself, that is to say it not only bears the component to be mounted. Rather, the positionally fixed sleeve also serves as the braking element itself, by way of which the rotatably mounted component can be braked. For this purpose, according to the invention, a pressure element is provided in the interior of the sleeve. Through the use of the pressure element, a pressure can be exerted on the sleeve at the inner side of the sleeve, in such a way that the sleeve is expanded radially, albeit slightly. In this way, an air gap that exists between the outer side of the sleeve and the component, or the inner side of the bearing eyelet on the component, is bridged. In other words, with sufficient internal pressure and expansion of the sleeve, the outer side of the sleeve comes into frictional contact with the component or with the inner side of the bearing eyelet. Consequently, frictional engagement, and braking of the component, are realized.

Since the frictional engagement is realized only between the sleeve and the component, and the pressure element itself serves merely for imparting the required internal pressure, it is consequently the case that the pressure element is not at any time subjected to the braking or friction torque itself, so that the pressure element is not in any way impeded by the braking process itself.

Since the pressure element is integrated into the sleeve that forms the bearing axle, it is consequently the case that an extremely compact construction of the bearing configuration is realized, in such a way that a bearing configuration of this type can be integrated even in a very small structural space. At the same time, a very high braking torque can be transmitted, which, depending on the construction of the bearing configuration, may amount to several tens of Nm to several hundred Nm.

The air gap itself should be as narrow as possible, and should have a width of between 5 µm and 500 µm, in particular between 10 µm and 200 µm. The size of the air gap is ultimately dependent on the deformability of the sleeve and on the pressure that can be generated by way of the pressure element.

The pressure element itself may be a hydraulically or pneumatically or mechanically operating element. A hydraulically or pneumatically operating element has, for example, a cylinder section and a piston, in which the piston is moved in the hydraulic-fluid-filled or gas-filled cylinder for the purposes of pressure generation. In this case, the cylinder wall expands and presses against the interior of the sleeve, which leads to the expansion of the sleeve. Alternatively, it is also possible for a mechanism to be provided which is externally actuated and by way of which the pressure element is radially expanded for the purposes of pressure generation. For example, a movable cone is conceivable which is pressed into a recess of compatible shape defined by way of multiple radially movable segments, in such a way that the segments are displaced radially. Disk springs or spring packs which, under load, expand radially and act on the shell of the pressure element are also conceivable.

In the same way as the basic mode of operation of the pressure element itself may differ, different measures for actuating the pressure element are also conceivable. The pressure element is externally actuated. In a first alternative of the invention, the pressure element may be hydraulically or pneumatically actuated. That is to say, a corresponding hydraulic or pneumatic system is provided which can be correspondingly actuated or controlled by the user and which in turn actuates the pressure element in accordance with the construction thereof.

In this context, it is for example possible for a pressure-generating device to be provided, by way of which a pressure can be hydraulically or pneumatically exerted on the pressure element for the actuation thereof. The pressure-generating device, a suitable pump, is for example connected to an input of the pressure-generating element through a corresponding hydraulic or pneumatic line. If the pump is actuated by the operator, a corresponding pressure is generated, in such a way that the pressure-generating element is actuated and the braking process is initiated.

As an alternative to this, the pressure element may also be actuable by an electric motor. For this purpose, it is expediently the case that an electric motor is provided by way of which the pressure element is actuable directly or through an actuation mechanism. The electric motor may, for example, be coupled directly to the pressure element, in accordance with the construction thereof in terms of function. The electric motor may thus act directly on the piston, described by way of example in the introduction, of the pressure element or the like. Alternatively, the electric motor may also be positioned externally with respect to the pressure element and coupled thereto by way of a corresponding actuation mechanism, for example one or more suitable rods or levers, in such a way that a movement of the electric motor leads to a corresponding movement of the actuation mechanism and thus an actuation of the pressure element.

The actuation of the pressure-generating element or of the electric motor is preferably remote-controllable. This makes it possible for the operator to actuate or release the brake even from a distance. As an alternative to this, a direct manual actuation of the pressure-generating element, that is to say of the pump of the electric motor, is self-evidently also conceivable.

In a third alternative, the pressure element may finally be mechanically actuable. In this case, therefore, the pressure element, in accordance with the construction thereof in terms of function, is actuated by way of a pure actuation mechanism. For this purpose, a manual actuation element, in particular in the form of a lever, may be provided, which is actuated by the operator. The actuation element, that is to say for example the lever, may then act directly on the pressure element, that is to say it may be coupled directly thereto.

Alternatively, the actuation element, that is to say for example the lever, may also be coupled to the pressure element through an actuation mechanism in the form of one or more connecting rods or the like. If necessary, it is possible through an actuation mechanism of this type—and this also applies in the case of a coupling of the electric motor through an actuation mechanism—for a transmission ratio to be realized in order to yet further increase the actuation force.

The component itself which is mounted on the sleeve is preferably a toothed wheel or a toothed wheel segment. The toothed wheel or toothed wheel segment meshes, for example, with a further toothed wheel or toothed wheel segment which is to be arrested and which is in turn connected to the component which is to be braked by way of the bearing configuration. The bearing configuration thus serves in this case both for the mounting of the toothed wheel as well as for a brake device for an external component which is to be braked, which component is connected by way of its own toothed wheel or toothed wheel segment to that of the bearing configuration. Such a component associated with the bearing configuration may for example be the C-arm, which is pivotable about a vertical axis and is part of a medical examination device.

Aside from the bearing configuration itself, the invention also relates to a medical examination device. Therefore, with the objects of the invention in view, there is also provided a medical examination device, comprising a C-arm together with a radiation source and a radiation receiver. The C-arm is rotatably mounted on a device frame and the C-arm is associated with a bearing configuration of the type described above. An example of the integration of a bearing configuration of this type is a medical examination device in the form of a C-arm system. A C-arm system of this type includes a radiation source and a radiation receiver which are disposed on the C-arm. The C-arm is in turn movable about multiple axes relative to a device frame. Normally, a C-arm of this type can be pivoted orbitally (along the C-arc), angularly (about a horizontal axis) and about a vertical axis (swivel axis), wherein the three axes are orthogonal to one another. One axis with which a bearing configuration of this type can be associated is, for example, the vertical axis, that is to say the swivel axis.

Through the use of this bearing configuration, the C-arm can be braked and arrested as required. For this purpose, the bearing configuration component which can be braked is mechanically coupled to the C-arm, in such a way that the braking of the component inevitably also brakes the C-arm movement.

The bearing axis of the bearing configuration is expediently parallel to the axis of rotation of the C-arm, wherein the two axes are preferably vertical axes.

The C-arm expediently has a toothed wheel or a toothed wheel segment, the bearing configuration also has, as a component, a corresponding toothed wheel or toothed wheel segment, and the toothed wheels or toothed wheel segments mesh with one another. If the toothed wheel on the bearing configuration is braked and arrested by way of the integrated brake device, the C-arm is inevitably also braked.

Other features which are considered as characteristic for the invention are set forth in the appended claims.

Although the invention is illustrated and described herein as embodied in a bearing configuration for the rotational mounting of a component provided for rotational movement and a medical examination device including the bearing configuration, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
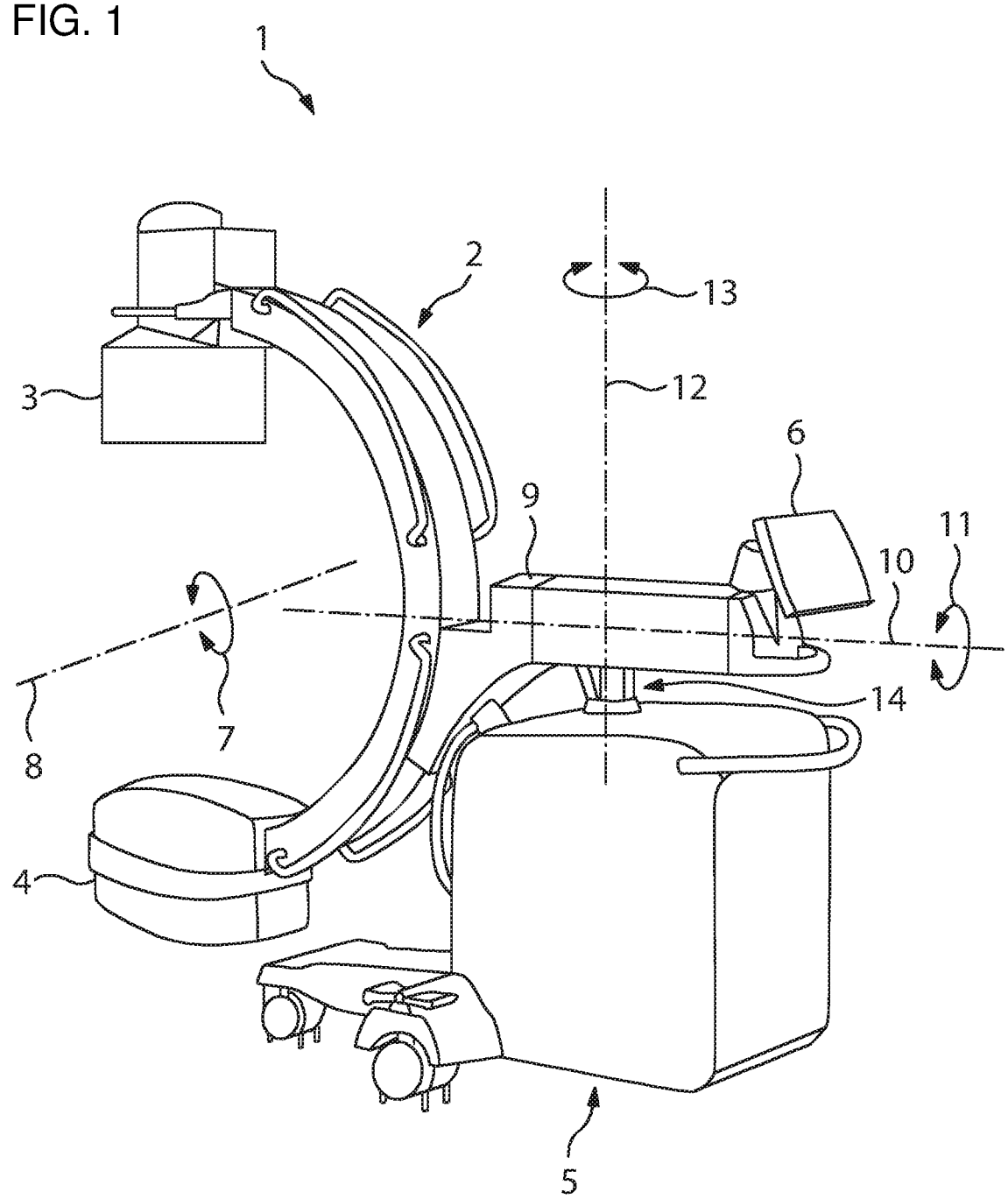
FIG. 1 is a diagrammatic, perspective view of a medical examination device according to the invention in the form of a C-arm system.

Referring now to the figures of the drawings in detail and first, particularly, to FIG. 1 thereof, there is seen a medical examination device according to the invention in the form of a C-arm system 1, which is constructed as an x-ray device. An x-ray source 3 and an x-ray radiation detector 4 are disposed, so as to be situated opposite one another, on the ends of a C-arm 2. The radiation source 3 emits x-ray radiation for the fluoroscopy of a patient positioned between the x-ray source 3 and the x-ray radiation detector 4. The x-ray radiation detector 4 receives the emitted x-ray radiation and generates a fluoroscopic image of the patient.

The C-arm 2 is disposed on a device part or frame 5 wherein, in the example, the entire system is mounted by way of roller bearings and can be moved correspondingly. The system can be operated correspondingly by way of an operating device 6.

The C-arm 2 is rotatable or pivotable about multiple axes. In FIG. 1, an arrow 7 shows a rotation about a horizontal orbital axis 8. A joint 9 is provided above the device frame 5 for pivoting the C-arm 2 about a horizontal angle axis 10, as illustrated by an arrow 11. Furthermore, the C-arm 2 is rotatable about a vertical axis of rotation 12, a so-called swivel axis, as is illustrated by an arrow 13. The respective axes are orthogonal with respect to one another.

In order to enable the C-arm 2 to be pivoted about the vertical axis 12 relative to the device frame 5, a corresponding bearing device 14 is provided by way of which the C-arm 2 is mounted rotatably relative to the device frame 5. The pivoting about the axis of rotation 12 may be performed manually or automatically. A device is provided in the region of the bearing device 14, which makes it possible for the pivoting movement to be braked and arrested.

Figure 2:
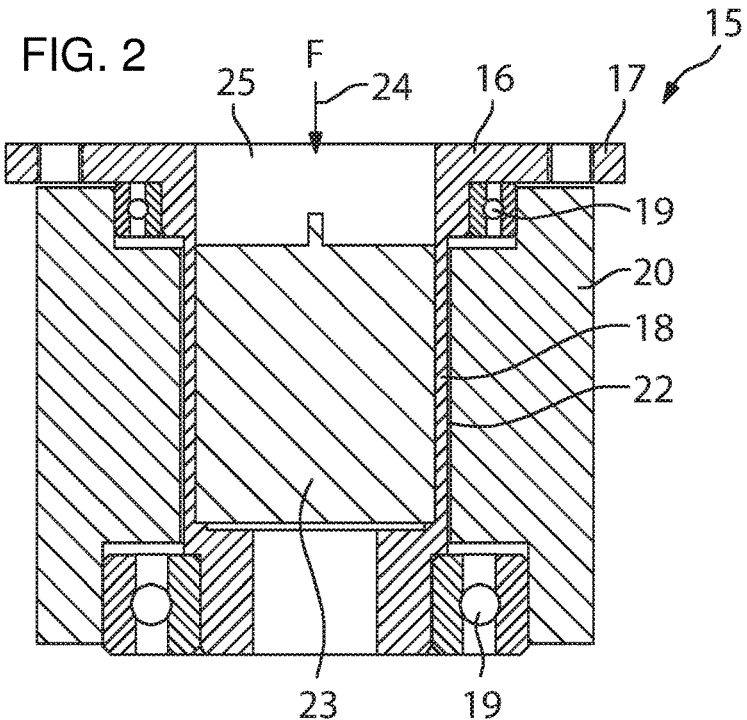
FIG. 2 is a longitudinal-sectional view of a bearing configuration according to the invention.
Figure 3:
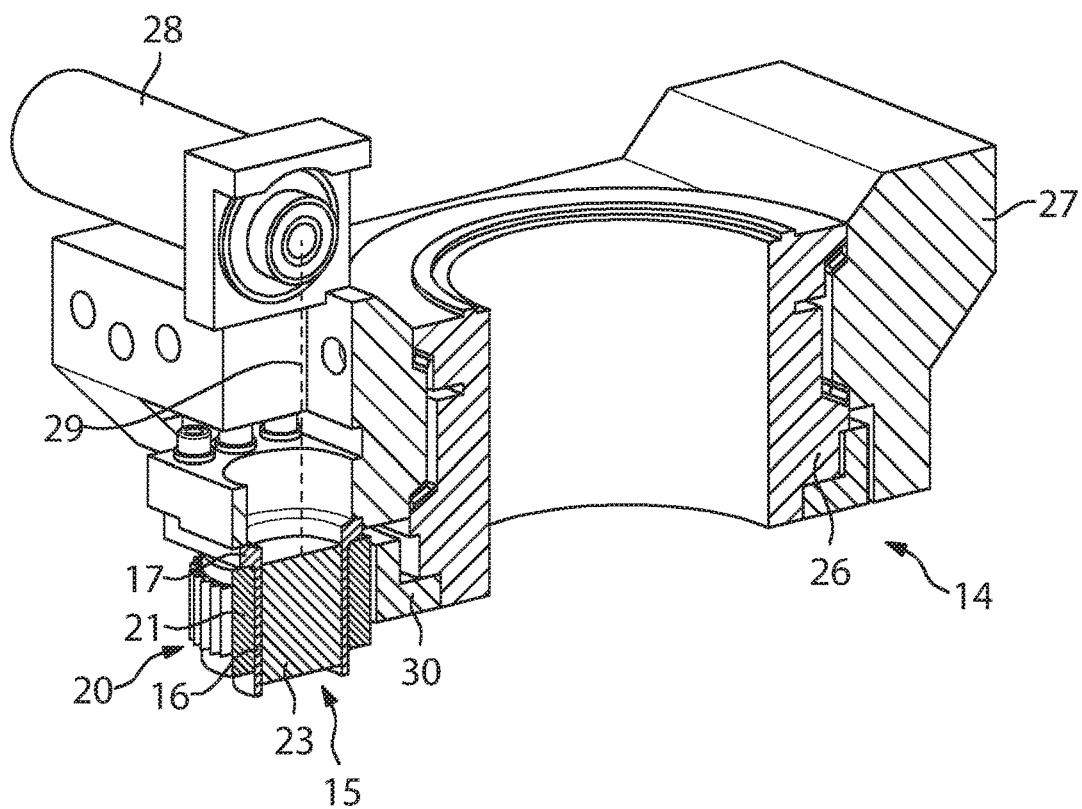
FIG. 3 is a partly sectional, perspective view of the examination device of FIG. 1, illustrating a rotational mounting of the C-arm about a vertical axis and an associated bearing configuration for braking and arresting the C-arm.

Such a device is shown in FIG. 2 in the form of a bearing configuration 15 according to the invention. The bearing configuration 15 includes a positionally fixed sleeve 16 which is positionally fixed relative to the device frame 5, for example by way of a suitable bearing flange 17. The sleeve 16 has a relatively thin-walled sleeve section 18 and the sleeve itself has a hollow cylindrical form. A component 20 which is to be rotatably mounted is, for example, an externally-toothed toothed wheel 21 as is seen in FIG. 3. In the illustrated example, the component 20 is rotatably mounted on the sleeve 16 by way of two rolling bearings 19. As an alternative to the illustrated mounting of the component 20 by way of the two rolling bearings 19, it would likewise be conceivable for the component 20 to be mounted in plain-bearing fashion on the sleeve 16. In this case, the two rolling bearings 19 would be omitted. This necessitates that the sleeve 16 be manufactured from a corresponding material such as, for example, brass.

The outer diameter of the sleeve 16 in the region of the thin-walled sleeve section 18 and the inner diameter of the component 20 in the region situated opposite are selected in such a way that a very narrow bearing gap 22 remains between them. This bearing gap has a width of a few micrometers and the width thereof should preferably lie between 5 and 500 µm, preferably between 10 and 200 µm.

A pressure element 23, which likewise has a cylindrical form, is received in the interior of the sleeve 16. This pressure element is dimensioned, in terms of its outer diameter, so as to bear preferably in a form-locking fashion against the inner wall of the sleeve. As is shown in FIG. 2, the pressure element is positioned in particular in the region of the thin-walled sleeve section 18. The braking action of the bearing configuration 15 can now be realized by way of the pressure element 23.

For this purpose, the pressure element 23 is capable, when actuated, of generating a radial force, that is to say expanding radially, in such a way that, by way of the pressure element 23, a pressure is exerted on the inner side of the thin-walled sleeve section 18. The latter follows the internal pressure and, in turn, expands radially. This has the effect that the bearing gap 22 is bridged, in such a way that the outer side of the thin-walled sleeve section 18 comes into frictional contact with the inner side of the component 20. Friction and frictional engagement are realized, so that the rotating component 20 is braked since, as described, the sleeve 16 is positionally fixed. A fully arresting action is realized with sufficiently intense frictional engagement. If the pressure is released again, that is to say the pressure element 23 is no longer actuated, the expanded sleeve section 18 relaxes again, the component 20 is released again and can rotate in an unbraked fashion.

Figure 4:
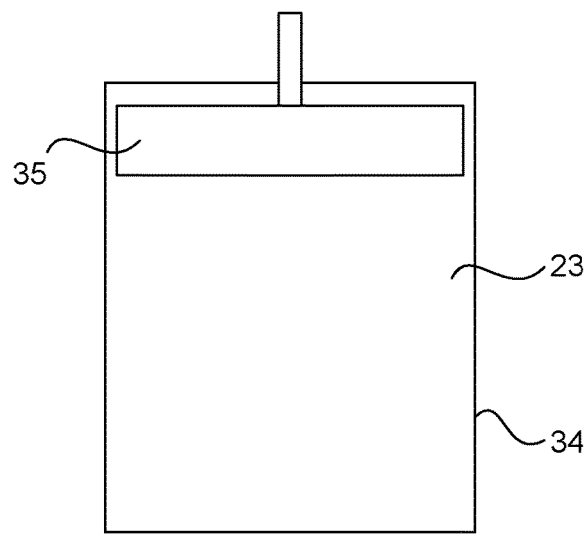
FIGS. 4 and 5 are longitudinal-sectional views of alternative embodiments of a pressure element.
Figure 5:
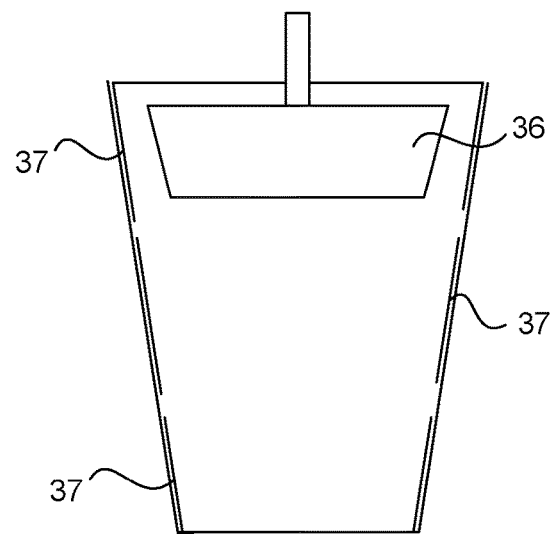

In order to generate the internal pressure, the pressure element 23 operates hydraulically, pneumatically or mechanically. The pressure element has an outer sleeve 34 which forms, for example, a cylinder as seen in FIG. 4. The cylinder is filled, for example, with hydraulic fluid or gas and a piston 35 protrudes into the cylinder. If the piston is moved in the cylinder an expansion of the cylinder, and thus the generation of the internal pressure, are realized. Alternatively, it is also possible for a mechanically operating pressure element 23 to be provided. In this case, for example, a conical piston 36 is moved into a corresponding receptacle formed from multiple radially movable segments 37 as seen in FIG. 5. The segments run against the element wall, whereby the corresponding expansion and thus generation of the internal pressure, are realized.

Figure 6:
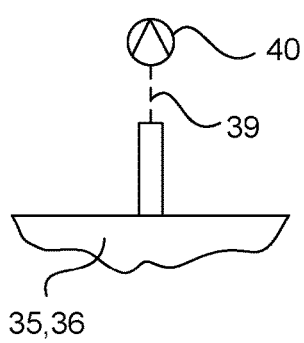
FIGS. 6, 7 and 8 are fragmentary, elevational views of alternative embodiments for actuating the pressure element.

In order to actuate the pressure element 23, a force F is exerted externally on the pressure element 23, as is illustrated by an arrow 24. Since the mode of operation of the pressure element 23 may also differ, it is also possible for the manner of force generation and/or force transmission to differ. For example, the force may be generated hydraulically or pneumatically. For this purpose, a pressure-generating device such as a pump 40 and a pressure line 39 are provided as seen in FIG. 6. The pressure line is coupled to an input 25 of the pressure element 23. If the pressure-generating element is actuated by an operator, for example by remote control, then a corresponding hydraulic pressure is generated by way of the pump 40 and the hydraulic pressure is transmitted through the hydraulic line 39 to the input 25. The pressure or the force leads to the actuation of the pressure element 23, in accordance with the construction thereof.

Figure 7:
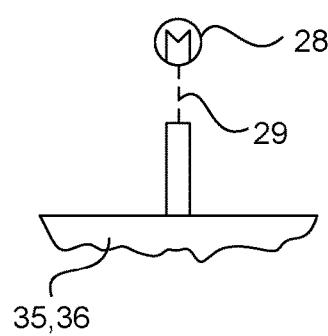

As an alternative to this, it is also possible for an electric motor 28 to be provided, which is shown in FIG. 7 and will be discussed in more detail below. This electric motor is, for example, connected to the input 25 through an actuation mechanism 29. When the motor is actuated, the actuation mechanism presses on the force input, and an actuation of the pressure element 23 occurs, in accordance with the construction thereof.

Figure 8:
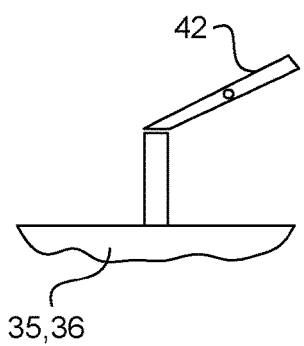

Finally, it is also possible for a purely mechanical actuating device to be provided, for example in the form of a lever 42 and/or of an actuation mechanism connected downstream. The operator actuates the lever, in such a way that the force introduced in this way is correspondingly transmitted to the input 25 as shown in FIG. 8.

FIG. 3 is a diagrammatic, sectional view showing a portion of the bearing device 14 by way of which the C-arm is mounted on the device frame 5 so as to be rotatable about the vertical axis 12. The figure shows a bearing sleeve 26 which is associated with the C-arm 2, that is to say the bearing sleeve is coupled to the C-arm 2, which is realized by way of the corresponding bearing arm as shown in FIG. 1. The bearing sleeve 26 is received, or rotatably mounted, in a suitable bearing receptacle 27 which is connected to the device frame 5, in such a way that the C-arm is ultimately mounted by way of the bearing sleeve 26 so as to be rotatable relative to the device frame 5.

The bearing configuration 15, which is provided on the bearing receptacle 27, serves for braking the rotation of the C-arm about the axis of rotation 12 according to the invention. For this purpose, the sleeve 16 is fixedly connected to the bearing receptacle 27 by way of the bearing or fastening flange 17. The pressure element 23 is situated in the interior of the sleeve 16. The illustration likewise shows the component 20, in this case in the form of the toothed wheel 21.

The illustration shows an electric motor 28 which is associated with the bearing configuration 15 and which is disposed in a suitable holder of the bearing receptacle 27. The electric motor 28 is connected by way of an actuation mechanism 29 (illustrated herein merely by dashed lines) to the force input 25 of the pressure element 23. If the electric motor 28 is actuated for example by way of remote control or by actuation of an operating button on the operating device 6, the electric motor rotates. The drive imparted by the electric motor has the effect that the actuation mechanism 29 actuates the pressure element 23. The pressure element generates the described internal pressure, and the sleeve 16 is expanded slightly in the region of the thin-walled sleeve section 18, resulting in frictional engagement with the toothed wheel 21.

The toothed wheel 21 in turn meshes with a toothed wheel 30 which is fastened to, that is to say rotates with, the sleeve 26. During normal operation, when the C-arm is to be pivoted about the axis of rotation 12, it is consequently the case that the sleeve 26 together with toothed wheel 30 rotates in the bearing receptacle 27. Since the toothed wheel 21 is released, it rotates jointly. However, if the rotational movement, which is normally performed only through a few angular degrees, for example +/−15° from a 0 position, is to be braked and arrested, the pressure element 23 is actuated by way of the electric motor 28. The toothed wheel 21 is braked due to the frictional engagement. This inevitably has the effect that the toothed wheel 30, and with it the bearing sleeve 26, and through the latter ultimately also the C-arm, are also braked. The braked end position is arrested for as long as the pressure element 23 is actuated. It is only when the frictional engagement is withdrawn and the toothed wheel 21 is released that the C-arm can rotate about the axis of rotation 12 again.

FIG. 3 shows, by way of example, a radially external configuration of the bearing configuration 15 relative to the components which are to be braked, that is to say in this case the bearing sleeve 26. It would, however, basically also be conceivable for the bearing configuration 15 to be integrated into the bearing sleeve 26, which would then have to be provided with a correspondingly internally toothed section.

The described exemplary embodiment with the C-arm system presents the use of the bearing configuration ultimately as a braking device. The bearing configuration serves for the mounting of the toothed wheel 21, which in turn serves as a braking element for a component coupled thereto, in this case the bearing sleeve 26. It is, however, basically also possible for the mounting of a corresponding component which is to be braked or arrested to be realized directly by way of the bearing configuration. For example, a pivot arm of an actuating device or the like may be mounted on the sleeve, the pivot arm thus being rotatably mounted by way of the bearing configuration. At the same time, the pivot arm can also be correspondingly braked and arrested by way of the bearing configuration 15. The possible uses of the bearing configuration 15 according to the invention are thus in no way restricted to the described embodiment, but are rather wide-ranging and usage is possible wherever a component is to be mounted and braked by way of the integrated brake.

Even though the invention has been illustrated and described in more detail on the basis of the preferred exemplary embodiment, the invention is not restricted by the disclosed examples, and other variations may be derived therefrom by a person skilled in the art, without departing from the scope of protection of the invention.

The invention claimed is:

1. A bearing configuration for rotationally mounting a component provided for rotational movement, the bearing configuration comprising:
   a positionally fixed sleeve having an interior;
   at least one bearing element or plain bearing rotatably mounting the component on said positionally fixed sleeve and defining an air gap between said positionally fixed sleeve and the component; and
   a pressure element disposed in said interior of said sleeve for radially expanding said sleeve and placing said sleeve in frictional contact with the component.

2. The bearing configuration according to claim 1, wherein said air gap has a width of between 5 μm and 500 μm.

3. The bearing configuration according to claim 1, wherein said air gap has a width of between 10 μm-200 μm.

4. The bearing configuration according to claim 1, wherein said pressure element is a hydraulically or pneumatically or mechanically operating element.

5. The bearing configuration according to claim 1, wherein said pressure element is hydraulically or pneumatically actuable.

6. The bearing configuration according to claim 5, which further comprises a pressure-generating device for hydraulically or pneumatically exerting a pressure on said pressure element for actuation of said pressure element.

7. The bearing configuration according to claim 1, which further comprises an electric motor for actuating said pressure element.

8. The bearing configuration according to claim 7, wherein said pressure element is actuable by said electric motor directly or through an actuation mechanism.

9. The bearing configuration according to claim 6, wherein said pressure-generating device is actuated by remote control.

10. The bearing configuration according to claim 8, wherein said electric motor is actuated by remote control.

11. The bearing configuration according to claim 1, wherein said pressure element is mechanically actuable.

12. The bearing configuration according to claim 11, which further comprises a manual actuation element for actuating said pressure element directly or through an actuation mechanism.

13. The bearing configuration according to claim 12, wherein said manual actuation element is a lever.

14. The bearing configuration according to claim 1, wherein the component is a toothed wheel or a toothed wheel segment.

15. A medical examination device, comprising:
- a device frame;
- a C-arm;
- a bearing configuration according to claim 1 rotatably mounting said C-arm on said device frame; and
- a radiation source and a radiation receiver mounted on said C-arm.

16. The medical examination device according to claim 15, wherein said C-arm has an axis of rotation, and said bearing configuration has a bearing axis being parallel to said axis of rotation of said C-arm.

17. The medical examination device according to claim 16, wherein said bearing axis and said axis of rotation are vertical axes.

18. The medical examination device according to claim 15, wherein said C-arm has a toothed wheel or a toothed wheel segment, said bearing configuration has a toothed wheel or a toothed wheel segment, and said toothed wheels or toothed wheel segments mesh with one another.

\* \* \* \* \*